(12) United States Patent
Dellinger et al.

(10) Patent No.: US 7,524,950 B2
(45) Date of Patent: *Apr. 28, 2009

(54) USES OF CATIONIC SALTS FOR POLYNUCLEOTIDE SYNTHESIS

(75) Inventors: Douglas J. Dellinger, Boulder, CO (US); Eric LeProust, San Jose, CA (US); Bill Peck, Mountain View, CA (US); Marvin H. Caruthers, Boulder, CO (US); Peter Cogan, Boulder, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 668 days.

This patent is subject to a terminal disclaimer.

(21) Appl. No.: 11/117,884

(22) Filed: Apr. 29, 2005

(65) Prior Publication Data

US 2005/0287555 A1    Dec. 29, 2005

Related U.S. Application Data

(63) Continuation-in-part of application No. 10/001,044, filed on Oct. 31, 2001, now Pat. No. 6,852,850.

(51) Int. Cl.
C07H 21/00 (2006.01)
C07H 21/02 (2006.01)
C07H 21/04 (2006.01)

(52) U.S. Cl. ............... 536/25.3; 536/25.33; 536/25.34; 536/22.1; 536/23.1; 536/25.41

(58) Field of Classification Search .................. None
See application file for complete search history.

(56) References Cited

U.S. PATENT DOCUMENTS

| 5,449,754 | A | 9/1995 | Nishioka |
| 6,015,880 | A | 1/2000 | Baldeschwieler et al. |
| 6,852,850 | B2 * | 2/2005 | Myerson et al. ............... 506/16 |
| 6,858,720 | B2 * | 2/2005 | Myerson et al. ............ 536/25.3 |
| 2001/0044115 | A1 | 11/2001 | Perbost |
| 2003/0092904 | A1 | 5/2003 | Myerson et al. |
| 2005/0287555 | A1 | 12/2005 | Dellinger et al. |

* cited by examiner

*Primary Examiner*—Traviss C McIntosh, III

(57) ABSTRACT

Inkjet printhead solvents and methods of forming an addressable nucleotide array are disclosed.

28 Claims, 4 Drawing Sheets

USES OF CATIONIC SALTS FOR POLYNUCLEOTIDE SYNTHESIS

CROSS-REFERENCE TO RELATED APPLICATION

This application claims priority to and is a continuation-in-part application of: U.S. patent application entitled, "Use of Ionic Liquids for Fabrication of Polynucleotide Arrays", Ser. No. 10/001,044, filed Oct. 31, 2001, now U.S. Pat. No. 6,852,850, which is entirely incorporated herein by reference; U.S. patent application entitled "Method of Synthesizing Polynucleotides Using Ionic Liquids," having Ser. No. 09/999,623, filed Oct. 31, 2001, now U.S. Pat. No. 6,858,720, which is entirely incorporated herein by reference; U.S. application entitled, "Use of Ionic Liquids for Fabrication of Polynucleotide Arrays" to Myerson et al., Ser. No. 11/020,428, filed Nov. 22, 2004, now U.S. Pat. No. 7,435,810, which is entirely incorporated herein by reference; U.S. patent application entitled "Method of Synthesizing Polynucleotides Using Ionic Liquids," to Myerson et al., Ser. No. 11/020,408, filed Nov. 22, 2004, now U.S. Pat. No. 7,411,061, which is entirely incorporated herein by reference.

STATEMENT REGARDING FEDERALLY SPONSORED RESEARCH OR DEVELOPMENT

The U.S. government may have a paid-up license in this invention and the right in limited circumstances to require the patent owner to license others on reasonable terms as provided for by the terms of MDA n39998-01-9-7068 awarded by the DARPA of the U.S. Government.

BACKGROUND

Oligonucleotides or polynucleotides immobilized on planar substrates are increasingly useful as diagnostic or screening tools. Polynucleotide arrays include regions of usually different sequence oligonucleotides or polynucleotides arranged in a predetermined configuration on the substrate. These regions (sometimes referenced as "features") are positioned at respective locations ("addresses") on the substrate. The arrays, when exposed to a sample, will exhibit an observed binding pattern. This binding pattern can be detected upon interrogating the array. For example, all polynucleotide targets (e.g., DNA) in the sample can be labeled with a suitable label (such as a fluorescent compound), and the fluorescence pattern on the array can be accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Polynucleotide arrays can be fabricated by depositing previously obtained polynucleotides onto a substrate, or by in situ synthesis methods. Various chemical schemes have been described for the synthesis of polynucleotides. Typically these methods use a nucleoside reagent of the formula:

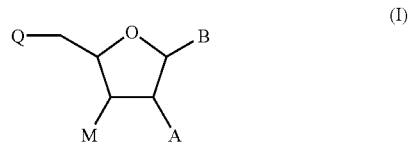

in which:
  A represents H or an optionally protected hydroxyl group;
  B is a purine or pyrimidine base whose exocyclic amine functional group is optionally protected;
  one of M or Q is a conventional protecting group for the 3' or 5'-OH functional group (or, optionally, a conventional 3' or 5'-OH protecting group at the end of an intervening (and optionally protected) polynucleotide sequence, e.g., such that formula (I) can represent a modified polynucleotide) while the other is:

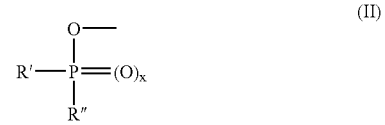

where x can be 0 or 1, provided that:
  a) when x=1:
  R' represents H and R" represents a negatively charged oxygen atom; or
  R' is an oxygen atom and R" represents either an oxygen atom or an oxygen atom carrying a protecting group; and
  b) when x=0, R' is an oxygen atom carrying a protecting group and R" is either a hydrogen, halogen, or a di-substituted amine group.

When x is equal to 1, R' is an oxygen atom and R" is an oxygen atom, the method is in this case the so-called phosphodiester method; when R" is an oxygen atom carrying a protecting group, the method is in this case the so-called phosphotriester method.

When x is equal to 1, R' is a hydrogen atom and R" is a negatively charged oxygen atom, the method is known as the H-phosphonate method.

When x is equal to 0, R' is an oxygen atom carrying a protecting group and R" is a halogen, the method is known as the phosphite method, and when R" is a leaving group of the disubstituted amine type, the method is known as the phosphoramidite method.

The conventional sequence used to prepare an oligonucleotide using reagents of the type of formula (I), basically follows four separate steps: (a) coupling a selected nucleoside which also has a protected hydroxy group, through a phosphite linkage to a functionalized support in the first iteration, or a nucleoside bound to the substrate (e.g., the nucleoside-modified substrate) in subsequent iterations; (b) optionally, but preferably, blocking unreacted hydroxyl groups on the substrate bound nucleoside; (c) oxidizing the phosphite linkage of step (a) to form a phosphate linkage; and (d) removing the protecting group ("deprotection") from the now substrate-bound nucleoside coupled in step (a), to generate a reactive site for the next cycle of these steps. The functionalized support (in the first cycle) or deprotected coupled nucleoside (in subsequent cycles) provides a substrate-bound moiety with a linking group for forming the phosphite linkage with a next nucleoside to be coupled in step (a). Final deprotection of nucleoside bases can be accomplished using alkaline conditions, such as ammonium hydroxide, in a known manner.

The in situ method for fabricating a polynucleotide array typically follows, at each of the multiple different addresses at which features are to be formed, the same conventional iterative sequence used in forming polynucleotides on a support by means of known chemistry. During array fabrication, different monomers can be deposited at different addresses on the substrate during any one iteration so that the different features of the completed array will have different desired polynucleotide sequences. The coupling can be performed by depositing drops of an activator and phosphoramidite at the specific desired feature locations for the array. One or more intermediate further steps can be required in each iteration, such as the conventional oxidation and washing steps.

The foregoing methods of preparing polynucleotides are well known and described in detail, for example, in Caruthers, Science 230: 281-285, 1985; Itakura et al., Ann. Rev. Biochem. 53: 323-356; Hunkapillar et al., Nature 310: 105-110, 1984; and in "Synthesis of Oligonucleotide Derivatives in Design and Targeted Reaction of Oligonucleotide Derivatives, CRC Press, Boca Raton, Fla., pages 100 et seq., U.S. Pat. Nos. 4,415,732, 4,458,066, 4,500,707, 5,153,319, 5,869,643, EP 0294196, and elsewhere. The phosphoramidite and phosphite triester approaches are most broadly used, but other approaches include the phosphodiester approach, the phosphotriester approach and the H-phosphonate approach. Such approaches are described in Beaucage et al., Tetrahedron (1992) 12:2223-2311. A more recent approach for synthesis of polynucleotides is described in U.S. Pat. No. 6,222,030 B1 to Dellinger et al., issued Apr. 24, 2001.

Although much research has been directed towards improving the feasibility and outcome of the various steps in the synthetic cycle, the basic strategy has not changed in the last 20 years. While the methodology would, therefore, appear to be rather well founded and time tested, new avenues of research in the blossoming fields of molecular biology and diagnostic medicine are continually pioneering novel applications of the technology. Along with these new applications has come an urgent demand for a synthetic method of much broader scope which will allow for the generation of high purity, long sequence DNA on unique and varied surfaces. Of equal gravity is the reality that the untold myriad of present and future applications of solid phase DNA synthesis will often be constrained by extreme physical parameters which are incongruent with the established (yet narrow) set of phosphoramidite compatible reagents and solvents. One such incompatibility is manifest as the unacceptable background fluorescence resulting from unwanted reagent interactions with the glass surfaces employed for many DNA microarrays. The source of the residual fluorescence is poorly understood but the ultimate result is loss of sensitivity in assays that rely on fluorescence reporting of DNA binding. The situation is utterly unacceptable in the field of diagnostic medicine where false negative or false positive results can wholly negate the benefit of the technology.

A second concern with the manufacture of DNA microarrays is that of the rapid, efficient, accurate, and reproducible synthesis of DNA features on derivatized glass substrates. The demands of large scale production of microarrays is forcing the industry to investigate new paradigms of allocating reagents on the substrates. One current method of delivering the reagents consists of jetting them out of inkjet print heads. While commercial grade inkjet heads have thus far sufficed for proof of concept pilot productions, growing requirements for speed and precision are now clearly demanding more efficient and reliable hardware. Unfortunately, the more attractive industrial inkjet heads, which would appear to offer all of the attributes wanting in their less robust counterparts, require highly viscous inks in order to operate.

While viscosity is not generally an insurmountable physical constraint, the problem becomes more apparent when one considers that there is a very limited set of solvents, which support phosphoramidite coupling to a satisfactory degree. Only highly polar, aprotic solvents support the reaction, but the list of candidates is most notably constrained by the requirement for >99% efficiency in each subsequent coupling step. Otherwise attractive solvents are of no use in an arena where the final oligomeric product must be devoid of any deletions, mutations, or other errors attributed to inefficient coupling. Most disconcerting is the fact that most solvents or solutes that can be expected to increase the viscosity of a useful solvent are either polymers (ethylene glycols) or polyols (i.e. glycerol) which either retard the reaction or act as substrates, which consume the phosphoramidite.

Therefore, there is a need in the art to address the aforementioned deficiencies and shortcomings.

SUMMARY

Briefly described, embodiments of this disclosure include inkjet printhead solvents and methods of forming an addressable nucleotide array. One exemplary method of forming an addressable nucleotide array, among others, includes: providing a first nucleotide compound selected from a nucleotide, an oligonucleotide, and a polynucleotide, wherein the first nucleotide compound is dissolved in a first solution including a first co-solvent and a second co-solvent, wherein the first co-solvent comprising an organic salt, wherein the organic salt comprises a substituted heterocyclic organic cation and an anion, wherein the organic salt has a pKa of about 6 to 8, wherein the organic salt does not reduce the reaction characteristics of the first solution, wherein the first solution has a viscosity of about 5 to 20 cP and a surface tension of about 25 to 45 mN/m at a temperature of about 30 to 40° C.; disposing the first solution onto a first position on a substrate, wherein a structure is disposed in the first position, wherein the structure has a second nucleotide compound disposed thereon, wherein the second nucleotide compound is selected from a nucleotide, an oligonucleotide, and a polynucleotide; and disposing a second solution on the first position of the substrate, wherein the second solution includes an activator, wherein the activator initiates the formation of a third nucleotide including the first nucleotide compound and the second nucleotide compound.

Another exemplary method of forming an addressable nucleotide array, among others, includes: providing a first nucleotide compound selected from a nucleotide, an oligonucleotide, and a polynucleotide, wherein the first nucleotide compound is dissolved in a first solution including a first solvent, wherein the first solvent comprising an organic salt, wherein the organic salt comprises a substituted heterocyclic organic cation and an anion, wherein the first solution has a viscosity of about 5 to 20 cP and a surface tension of about 25 to 45 mN/m at a temperature of about 30 to 40° C.; disposing the first solution onto a first position on a substrate, wherein a structure is disposed in the first position, wherein the structure has a second nucleotide compound disposed thereon, wherein the second nucleotide compound is selected from a nucleotide, an oligonucleotide, and a polynucleotide; and disposing a second solution on the first position of the substrate, wherein the second solution includes an activator, wherein the activator initiates the formation of a third nucleotide including the first nucleotide compound and the second nucleotide compound.

One exemplary inkjet printhead solvent, among others, includes: an organic salt including a substituted heterocyclic organic cation and an anion, wherein the organic salt has a pKa of about 6 to 8, wherein the first solution has a viscosity of about 5 to 20 cP and a surface tension of about 25 to 45 mN/m at a temperature of about 30 to 40° C., wherein a first nucleotide compound is dissolved in a first solution including the organic salt.

Additional objects, advantages, and novel features of this disclosure shall be set forth in part in the descriptions and examples that follow and in part will become apparent to those skilled in the art upon examination of the following specifications or can be learned by the practice of the disclosure. The objects and advantages of the disclosure can be realized and attained by means of the instruments, combinations, compositions and methods particularly pointed out in the appended claims.

BRIEF DESCRIPTION OF THE DRAWINGS

Reference is now made to the following drawings. Note that the components in the drawings are not necessarily to scale.

DETAILED DESCRIPTION

Figure 1:
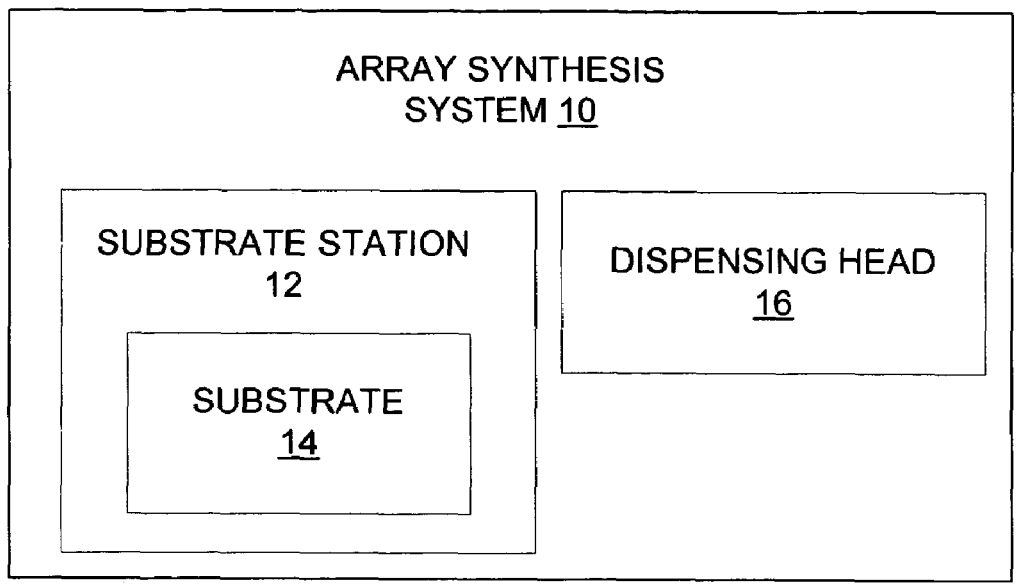
FIG. 1 illustrates an embodiment of an array synthesis system.

Embodiments of the present disclosure will employ, unless otherwise indicated, techniques of synthetic organic chemistry, biochemistry, molecular biology, and the like, that are within the skill of the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an" and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, polynucleotides include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a non-naturally occurring or synthetic base.

A "nucleotide" refers to a sub-unit of a nucleic acid (whether DNA or RNA or analogue thereof) which includes a phosphate group, a sugar group and a nitrogen containing base, as well as analogs of such sub-units.

A "nucleoside" references a nucleic acid subunit including a sugar group and a nitrogen containing base. It should be noted that the term "nucleotide" is used herein to describe embodiments of the disclosure, but that one skilled in the art would understand that the term "nucleoside" and "nucleotide" are interchangable in most instances. One skilled in the art would have the understanding that additional modification to the nucleoside may be necessary and one skilled in the art has such knowledge.

A "nucleoside moiety" refers to a molecule having a sugar group and a nitrogen containing base (as in a nucleoside) as a portion of a larger molecule, such as in a polynucleotide, oligonucleotide, or nucleoside phosphoramidite.

A "nucleotide monomer" refers to a molecule which is not incorporated in a larger oligo- or poly-nucleotide chain and which corresponds to a single nucleotide sub-unit; nucleotide monomers can also have activating or protecting groups, if such groups are necessary for the intended use of the nucleotide monomer.

A "polynucleotide intermediate" references a molecule occurring between steps in chemical synthesis of a polynucleotide, where the polynucleotide intermediate is subjected to further reactions to get the intended final product (e.g., a phosphite intermediate, which is oxidized to a phosphate in a later step in the synthesis), or a protected polynucleotide, which is then deprotected.

An "oligonucleotide" generally refers to a nucleotide multimer of about 2 to 100 nucleotides in length, while a "polynucleotide" includes a nucleotide multimer having any number of nucleotides.

It will be appreciated that, as used herein, the terms "nucleoside" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base can also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond can include a phospho or phosphite group, and can include linkages where one or more oxygen atoms of the phospho or phosphite group are either modified with a substituent or replaced with another atom, e.g. a sulfur atom, or the nitrogen atom of a mono- or di-alkyl amino group.

An "array", unless a contrary intention appears, includes any one, two or three dimensional arrangement of addressable regions bearing a particular chemical moiety or moieties (for example, polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature can incidentally detect non-targets of that feature). In the case of an array, the "target" will be referenced as a moiety in a mobile phase (typically fluid), to be detected by probes ("target probes") which are bound to the substrate at the various regions. However, either of the "target" or "target probes" can be the one which is to be evaluated by the other (thus, either one could be an unknown mixture of polynucleotides to be evaluated by binding with the other). While probes and targets of the present disclosure will typically be single-stranded, this is not essential. An "array layout" refers to one or more characteristics of the array, such as feature positioning, feature size, and some indication of a moiety at a given location. "Hybridizing" and "binding", with respect to polynucleotides, are used interchangeably.

A "group" includes both substituted and unsubstituted forms. Typical substituents include one or more lower alkyl, any halogen, hydroxy, or aryl, or optionally substituted on one or more available carbon atoms with a nonhydrocarbyl substituent such as cyano, nitro, halogen, hydroxyl, or the like. Any substituents are typically chosen so as not to substantially adversely affect reaction yield (for example, not lower it by more than 20% (or 10%, or 5% or 1%) of the yield otherwise obtained without a particular substituent or substituent combination). An "acetic acid" includes substituted acetic acids such as di-chloroacetic acid (DCA) or tri-chloroacetic acid (TCA).

A "phospho" group includes a phosphodiester, phosphotriester, and H-phosphonate groups. In the case of either a phospho or phosphite group, a chemical moiety other than a substituted 5-membered furyl ring can be attached to O of the phospho or phosphite group which links between the furyl ring and the P atom.

A "protecting group" is used in the conventional chemical sense to reference a group, which reversibly renders unreactive a functional group under specified conditions of a desired reaction. After the desired reaction, protecting groups can be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment.

A "hydroxyl protecting group" refers to a protecting group where the protected group is a hydroxyl. A "reactive-site hydroxyl" is the terminal 5'-hydroxyl during 3'-5'polynucleotide synthesis and is the 3'-hydroxyl during 5'-3'polynucleotide synthesis. An "acid labile protected hydroxyl" is a hydroxyl group protected by a protecting group that can be removed by acidic conditions. Similarly, an "acid labile protecting group" is a protecting group that can be removed by acidic conditions. Preferred protecting groups that are capable of removal under acidic conditions ("acid-labile protecting groups") include those such as tetrahydropyranyl groups, e.g. tetrahydropyran-2-yl and 4-methoxytetrahydropyran-2-yl; an arylmethyl group with n aryl groups (where n=1 to 3) and 3-n alkyl groups such as an optionally substituted trityl group, for example a monomethoxytrityl for oligoribonucleotide synthesis and a dimethoxytrityl for oligodeoxyribonucleotide synthesis, pixyl; isobutyloxycarbonyl; t-butyl; and dimethylsilyl. A trityl group is a triphenylmethyl group. Suitable protecting groups are described in "Protective Groups in Organic Synthesis" by T. W. Green, Wiley Interscience.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to eight carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "aryl" as used herein refers to an aromatic species containing 1 to 5 aromatic rings, either fused or linked, and either unsubstituted or substituted with 1 or more substituents typically selected from the group consisting of amino, halogen and lower alkyl. Preferred aryl substituents contain 1 to 3 fused aromatic rings, and particularly preferred aryl substituents contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —$(CH_2)_j$—Ar, wherein j is an integer in the range of 1 to 24, more typically 1 to 6, and Ar is a monocyclic aryl moiety.

Discussion

Embodiments of the present disclosure include methods for fabricating addressable biopolymer (e.g., a polynucleotide or a polypeptide) arrays, solutions including an organic salt used to prepare the biopolymer arrays, and inkjet systems using the solutions to fabricate the biopolymer arrays, all of which have numerous advantages relative to prior methods such as those discussed above. In general, the methods involve forming a target biopolymer (hereinafter "target polynucleotide") in the presence of a solvent or co-solvents, where the solvent or one of the co-solvents is an organic salt. In general, the organic salt includes an organic cation and either an inorganic or organic counterion (anion). While the organic salts can be used to alter the physical characteristics of the solution (e.g., viscosity, surface tension, and/or contact angle), the organic salts do not appreciably reduce the reaction characteristic (e.g., reactivity of the nucleotide compounds, rate of reaction of the nucleotide compounds, deblocking protecting groups and freeing alternative reaction sites, and buffering or neutralizing the acid catalyst) of the solution. Although both polynucleotide and polypeptides are contemplated to be included in embodiments of this disclosure, but for reasons of clarity, polynucleotides will be referred to for the remainder of the disclosure.

In particular, embodiments of the present disclosure provide methods of generating addressable arrays of polynucleotides on a substrate, where one or more of the solutions used to prepare the polynucleotide compounds include the organic salt as a solvent or co-solvent. Embodiments of this method include a solution having a nucleotide composition (e.g., a nucleoside, a nucleotide, an oligonucleotide, or a polynucleotide) dissolved in a solvent/co-solvent including the organic salt. The solution is then contacted with an array substrate to form an oligonucleotide or a polynucleotide, and in an iterative manner, the target polynucleotide of interest can be fabricated using one or more solutions having one of the compounds dissolved therein.

As mentioned above, the solutions including the organic salt and methods described above are particularly useful for fabricating an addressable polynucleotide array by in situ synthesis of polynucleotides on the array substrate. In one such embodiment, at each of the multiple different addresses on the substrate (e.g., at least one hundred, at least one thousand, or at least ten thousand addresses), the in situ synthesis cycle is repeated so as to form the addressable array with the same or different polynucleotide sequences at one or more different addresses on the substrate. In the array forming method, the compounds to be coupled at respective addresses are dissolved in a solvent/co-solvent containing an organic salt and deposited as droplets at those addresses using, for example, an inkjet printing system. The polynucleotides can be produced by disposing solutions (e.g., selected from four solutions, each containing a different nucleotide) on particular addressable positions in a specific order in an iterative process.

The synthesis of polynucleotides has been well-studied, and methods incorporate both aqueous and organic solvents. It is well known that changing the solvent in a reaction system frequently affects the performance of the reaction, sometimes profoundly. The ionic nature of organic salts fundamentally differs from the molecular nature of the aqueous or organic solvents used in various steps of the polynucleotide synthesis cycle. Potential problems include changes of chemical mechanism, possibly favoring different products due to the ionic nature of the solvent. Stabilization of charged reaction intermediates due to interaction with the organic salt, or chemical reaction with components of the organic salt itself might be expected.

Despite the previously mentioned potential problems, embodiments of the present disclosure achieves coupling of nucleotide moieties via formation of an internucleotide bond in a solvent including the organic salt. Various advantages exist in performing the coupling reaction in a solvent including the organic salt. One advantage includes the hydrophobicity of the organic salt leads to reduced problems in dealing with hydrolysis of the reactants due to water in the reaction environment. Less solvent can be used to wash between coupling steps, and organic salt solvents can be recovered more easily, when compared to prior art methods. This can be useful in large-scale synthesis, where many washing steps and relatively large volumes of solvents are required. The organic salts can be used as enhancing agents, for example, as viscosity enhancing agents. Not only do a variety of organic salts act to augment the viscosity of phosphoramidite friendly solvents, but they also support the coupling reaction as either pure solvents or as co-solvents. The organic salts are also readily modified to instill other favorable qualities for use as solvents. In particular, a wide range of viscosities and surface tensions as well as contact angles with standard glass substrates that are conducive to controlled substrate delivery. Several families of organic salts are also fully miscible with the standard organic solvents that support phosphoramidite chemistry such as acetonitrile, propylene carbonate, and dimethyl carbonate. Many of the organic salts also exist as room temperature liquids with no measurable vapor pressure, allowing for delivery of picoliter sized drops, which do not evaporate upon jetting. Some organic salts have been developed that act as the acid catalyst required for efficient phosphoramidite coupling. These activating organic salts are also characterized by favorable viscosity, surface tension, and solubility characteristics, which make it an ideal solvent/co-solvent.

As mentioned above, the solution includes the organic salt that is able to dissolve the nucleotide composition. In addition, the solution can include one or more additional solvents (co-solvents). The solution has a viscosity of about 1 to 1000 cP, about 1 to 200 cP, about 5 to 20 cP, and about 15 to 20 cP, at a temperature of about 20 to 30° C. In addition, the solution has a surface tension of about 25 to 45 mN/m, about 25 to 40 mN/m, about 30 to 40 mN/m, and about 30 to 35 mN/m, at a temperature of about 20 to 30° C. Furthermore, the solution has a contact angle θ, which is the incident angle measured where the drop contacts the surface relative to the plane formed by the surface. The contact angle is specific for each solvent/surface pair: the contact angle can be changed by either changing the solvent composition or the surface energy of the surface. The contact angle (e.g., with a planar glass) is about 20 to 100°, about 30 to 90°, and about 45 to 70°, at a temperature of about 20 to 30° C. It should be noted the viscosity, the surface tension, and/or, the contact angle can be adjusted (i.e., tuned) by modifying the ratio of organic salt to co-solvent.

The organic salts do not reduce the reaction characteristic (e.g., reactivity of the nucleotide compounds, rate of reaction of the nucleotide compounds, deblocking protecting groups and freeing alternative reaction sites, and buffering or neutralizing the acid catalyst) of the solution. In one embodiment, the organic salt is a co-solvent with another co-solvent (i.e., propylene carbonate), and although the organic salt modifies the viscosity and surface tension of the solution, the reaction characteristics of the solution are not appreciably affected.

The organic salts have a pKa of about 6 to 8, about 6.5 to 7.5, about 6.8 to 7.2.

The organic salt includes an organic cation and either an inorganic or organic counterion (anion). The organic cation is preferably an N-substituted pyridine having the following structure:

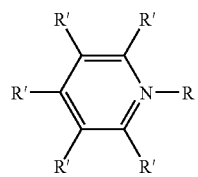

(A)

wherein R is alkyl (e.g., $C_2$ to $C_{10}$) and each R' is independently selected from hyrido, alkyl (e.g., $C_2$ to $C_{10}$), or halogen;

or a 1,3 di-substituted imidazole having the following structure:

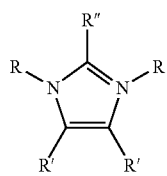

(B)

wherein each R is independently selected from alkyl, each R' is independently selected from hydrido, alkyl (e.g., $C_2$ to $C_{10}$), or halogen, and R" is selected from hydrido or methyl.

The 1,3 di-substituted imidazole organic cations include, but are not limited to, 1,3-dimethyl-imidazolium, 1-ethyl-3-methyl-imidazolium, 1-butyl-3-methyl-imidazolium, 1-hexyl-3-methyl-imidazolium, 1-decyl-3-methyl-imidazolium, 1-dodecyl-3-methyl-imidazolium, 1-methyl-3-octyl-imidazolium, 1-methyl-3-tetradecyl-imidazolium, 1,2-dimethyl-3-propyl-imidazolium, 1-ethyl-2,3-dimethyl-imidazolium, 1-butyl-2,3-dimethyl-imidazolium, and combinations thereof. In particular, the 1,3 di-substituted imidazole organic cations include 1-ethyl-3-methyl-imidazolium, 1-butyl-3-methyl-imidazolium, 1-dodecyl-3-methyl-imidazolium, 1-methyl 3-octyl-imidazolium, and combinations thereof.

The N-substituted pyridine organic cations include, but are not limited to, N-ethylpyridinium, N-butylpyridinium, N-hexylpyridinium, 4-methyl-N-butyl-pyridinium, 3-methyl-N-butyl-pyridinium, 4-methyl-N-hexyl-pyridinium, 3-methyl-N-hexyl-pyridinium, 4-methyl-N-octyl-pyridinium, 3-methyl-N-octyl-pyridinium, 3,4-dimethyl-N-butyl-pyridinium, and 3,5-dimethyl-N-butyl-pyridinium. In particular, the N-substituted pyridine organic cations include N-ethylpyridinium, N-butylpyridinium, and combinations thereof.

Embodiments of the anions of the organic salt include, but are not limited to, methylsulfate ($CH_3SO_4^-$), trifluoroacetate ($CF_3CO_2^-$), heptafluorobutanoate ($CF_3(CF_2)_2CO_2^-$), triflate ($CF_3SO_2^-$), nonaflate ($C_2F_5SO_2^-$), bis(trifluoromethylsulfonyl)imide (($CF_3SO_2)_2N^-$), bis(perfluoroethylsulfonyl)imide (($C_2F_5SO_2)_2N^-$), tysolate anion, dicyanimide anion, tris(trifluoromethylsulfonyl)methide (($CF_3SO_2)_3C^-$). In particular, the anion can be bis(trifluoromethylsulfonyl)imide (($CF_3SO_2)_2N^-$), and combinations thereof. Organic salts can be obtained from Covalent Associates (Woburn, Mass.), Aldrich Chemical Company Milwaukee, Wis.), Solvent Innovation (Köln, Germany), and Acros Organics (Geel, Belgium).

It should be noted that the amount of organic acid used depends, in part, upon the viscosity to be used for a particular embodiment. The lower limit for the weight % of the solution can be 0.01, 1, 2, 3, 4, 5, 10, 15, 20, 30, 40, 50, 60, 70, 80, and 90, while the upper limit can be 100, 90, 80, 70, 60, 50, 40, 30, 20, 15, 10, 5, 4, 3, 2, and 1.

As mentioned above, the organic salt can be a co-solvent that can be mixed with one or more other co-solvents. The other co-solvents can include solvents such as, but not limited to, acetonitrile, tetrahydrofuran, dimethylformamide, methylene chloride, propylene carbonate, adiponitrile, toluene, dioxane, dimethylsulfoxide, ethylene carbonate, diethyl carbonate, succinonitrile, N-methyl pyrrolidone, and combinations thereof. It should be noted that solvents such as sulfolane, nitromethane, nitrobenzene, and combinations thereof, that are not used in typical polynucleotide synthesis, can be used as co-solvents in embodiments of the present disclosure. In particular, the co-solvents include acetonitrile, propylene carbonate, adiponitrile, ethylene carbonate, and combinations thereof. Additional co-solvents that are not typically used in typical polynucleotide synthesis due to low and in most cases unacceptable yields include tetrahydrofuran, dimethylformamide, methylene chloride, adiponitrile, toluene, dioxane, dimethylsulfoxide, succinonitrile, N-methyl pyrrolidone, sulfolane, nitromethane, nitrobenzene, and combinations thereof.

As with the organic acid, it should be noted that the amount of co-solvent used depends, in part, upon the viscosity to be used for a particular embodiment. The lower limit for the weight % of the solution can be 0.01, 1, 2, 3, 4, 5, 10, 15, 20, 30, 40, 50, 60, 70, 80, and 90, while the upper limit can be 100, 90, 80, 70, 60, 50, 40, 30, 20, 15, 10, 5, 4, 3, 2, and 1.

As is known in the art, an activator is added to the solution to catalyze the formation of the internucleotide bond usually by the formation of a highly reactive intermediate. In phosphodiester, phosphotriester and H-phosphonate chemistry, Lewis Acid activators such as sulfonyl halides, sulfonyl azoles, pivaloyl halides, pivaloyl azoles, and adamatane carbonyl halides, are used to form mixed anhydrides that react to for the new internucleotide bond. In the case of phosphoramidite chemistry a protic acid catalyst is used to enhance the rate of displacement of the phosphorus-nitrogen bond. This rate can be additionally enhanced by using an azole catalyst that contains an acidic proton. Protic acid azole activator can include compounds such as, but not limited to, tetrazole, S-ethyl-thiotetrazole, 4-nitrotriazole, 5-benzylthio-tetrazole or dicyanoimidazole, although other acidic azoles can be used. An activator compound is typically included in a concentration of about 0.05 molar up to about 1.0 molar. The concentration of these activators depends, at least in part, on the solubility of the azole in a solvent that supports phosphoramidite coupling. However, a few of these activators can be dissolved at high concentrations in a variety of effective coupling solvents. At high concentrations, the acidic nature of these reagents typically cause undesired side reactions such as removal of acid labile protecting groups.

In an embodiment, the activator can include an organic salt such as those described above. In particular, the organic salt activator includes organic salts such as, but not limited to, methylimidazolium trifluoromethylsulfonyl imide, and combinations thereof. An organic salt activator compound is typically included in a concentration of about 0.05 molar up to about 1.0 molar.

In array fabrication, different nucleotide monomers and the activator can be deposited at different addresses on the substrate during any one cycle so that the different features of the completed array will have polynucleotides with different sequences. One or more intermediate further steps may be required in each cycle, such as the conventional oxidation, capping, and washing steps in the case of in situ fabrication of polynucleotide arrays (e.g., these steps can be performed by flooding the array surface with the appropriate reagents).

Another embodiment of the disclosure can extend to include using organic salts as solvents elsewhere in the synthesis cycle to reduce or substantially eliminate the presence of water during oxidation and deprotection. Thus, for example, in polynucleotide array synthesis, this embodiment may allow the number of wash steps (with non-aqueous solvent) over all of the addresses on the surface of the array to be reduced, with potential concomitant savings in time and solvents.

Embodiments of the methods lend themselves to synthesis of polynucleotides on array substrates in either the 3'-to-5' or the 5'-to-3' direction. In the former case, the initial step of the synthetic process involves attachment of an initial nucleotide to the array substrate at the 3' position, leaving the 5' position available for covalent binding of a subsequent monomer. In the latter case, the initial step of the synthetic process involves attachment of an initial nucleotide to the array substrate at the 5' position, leaving the 3' position available for covalent binding of a subsequent monomer. Following synthesis, the polynucleotide can, if desired, be cleaved from the solid support. The details of the synthesis in either the 3'-to-5' or the 5'-to-3' direction will be readily apparent to the skilled practitioner based on the prior art and the disclosure contained herein.

In one embodiment, a monomer nucleotide phosphoramidite is dissolved in the solvent including the organic salt, and the resulting solution is deposited upon the surface of the planar substrate, and the process is repeated multiple times, analogous to conventional polynucleotide synthesis, to form the target polynucleotide of interest.

The disclosure also encompasses the formation of an intemucleotide bond between two polynucleotides or oligonucleotides, or between a polynucleotide and an oligonucleotide, resulting in an extended polynucleotide immobilized on the array surface. In such case, one of the polynucleotides or oligonucleotides is dissolved in the solvent including the organic salt, and the substrate to be contacted with the solution bears the other polynucleotide or oligonucleotide.

The skilled practitioner in the art will realize that one of the nucleotide moieties must be activated, as in a phosphoramidite. Such modification is well known in the art. The dislcosure also encompasses embodiments where the oligonucleotide or polynucleotide dissolved in the solvent include modified oligonucleotides or modified polynucleotides, especially where the modified oligo- or -polynucleotides are "activated", or more susceptible to bond formation. Such modification of the oligo- or poly-nucleotides can be accomplished using known chemistries previously used for immobilizing oligo- or polynucleotides to insoluble substrates. Examples of such modifications can be found in: *Polymer-supported Reactions in Organic Chemistry*, Hodge, P. & Sherrington, D. C., (John Wiley & Sons, New York, N.Y. 1980); *Advanced Organic Chemistry of Nucleic Acids*, Shabarova, Z. & Bogdanov, A., (VCH, Weinheim, Germany 1994), pages 531-545.

In certain embodiments, polynucleotide probes are arranged on the substrate either by immobilization (e.g. by covalent attachment of a pre-synthesized probe), or by synthesis of the probe on the substrate (in situ synthesis). In fabricating a polynucleotide array, typically each region on the substrate surface on which an array will be or has been formed ("array regions") is completely exposed to one or more reagents. For example, the array regions will often be exposed to one or more reagents to form a suitable layer on the surface, which binds to both the substrate and the polynucleotide. In in situ synthesis, the array regions will also typically be exposed to the oxidizing, deblocking, and optional capping reagents. Similarly, particularly in fabrication by depositing previously obtained oligonucleotides or polynucleotides, it may be desirable to expose the array regions to a suitable blocking reagent to block locations on the surface at which there are no features from non-specifically binding to the target.

The array may contain any number of features, generally including at least tens of features, usually at least hundreds, more usually thousands, and as many as a hundred thousand or more features. All of the features may be different, or some or all could be the same. Each feature carries a predetermined moiety or a predetermined mixture of moieties, such as a particular polynucleotide sequence or a predetermined mixture of polynucleotides. The features of the array can be arranged in any desired pattern (e.g. organized rows and columns of features, for example, a grid of features across the substrate surface); a series of curvilinear rows across the substrate surface (for example, a series of concentric circles or semi-circles of features, and the like). In embodiments where very small feature sizes are desired, the density of features on the substrate can range from at least about ten features per square centimeter, or at least about 35 features per square centimeter, or at least about 100 features per square centimeter, and up to about 1000 features per square centimeter, up to about 10,000 features per square centimeter, or up to 100,000 features per square centimeter. Each feature carries a predetermined nucleotide sequence (which includes the possibility of mixtures of nucleotide sequences).

In one embodiment, about 10 to 100 of such arrays can be fabricated on a single substrate (such as glass). In such embodiment, after the substrate has the polynucleotides on its surface, the substrate can be cut into substrate segments, each of which can carry one or two arrays. It will also be appreciated that there need not be any space separating arrays from one another. Where a pattern of arrays is desired, any of a variety of geometries can be constructed, including for example, organized rows and columns of arrays (for example, a grid of arrays, across the substrate surface), a series of curvilinear rows across the substrate surface (for example, a series of concentric circles or semi-circles of arrays), and the like.

The array substrate can take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 300 mm, usually about 4 mm to 150 mm, more usually about 4 mm to 125 mm; a width in the range about 4 mm to 300 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. The substrate surface onto which the polynucleotides are bound can be smooth or substantially planar, or have irregularities, such as depressions or elevations. The configuration of the array can be selected according to manufacturing, handling, and use considerations.

In array fabrication, the quantities of polynucleotide available are usually very small and expensive. Additionally, sample quantities available for testing are usually also very small and it is therefore desirable to simultaneously test the same sample against a large number of different probes on an array. Therefore, one embodiment of the invention provides for fabrication of arrays with large numbers of very small, closely spaced features. Arrays can be fabricated with features that can have widths (that is, diameter, for a round spot) in the range from a minimum of about 10 micrometers to a maximum of about 1.0 cm. In embodiments where very small spot sizes or feature sizes are desired, material can be deposited according to the invention in small spots whose width is in the range about 1.0 micrometer to 1.0 mm, usually about 5.0 micrometers to 0.5 mm, and more usually about 10 micrometers to 200 micrometers. Interfeature areas will typically (but not essentially) be present which do not carry any polynucleotide. It will be appreciated though, that the interfeature areas could be of various sizes and configurations.

Suitable substrates can have a variety of forms and compositions and can be derived from naturally occurring materials, naturally occurring materials that have been synthetically modified, or synthetic materials. Examples of suitable support materials include, but are not limited to, nitrocellulose, glasses, silicas, teflons, and metals (for example, gold, platinum, and the like). Suitable materials also include polymeric materials, including plastics (for example, polytetrafluoroethylene, polypropylene, polystyrene, polycarbonate, and blends thereof, and the like), polysaccharides such as agarose (e.g., that available commercially as Sepharose®, from Pharmacia) and dextran (e.g., those available commercially under the tradenames Sephadex® and Sephacyl®, also from Pharmacia), polyacrylamides, polystyrenes, polyvinyl alcohols, copolymers of hydroxyethyl methacrylate and methyl methacrylate, and the like.

FIG. 1 illustrates an embodiment of an array synthesis system 10 that uses organic salt solvents/co-solvents in the application to the deposition of nucleotide compounds to a suitable substrate (as described above), especially for the fabrication of polynucleotide arrays. The array synthesis system 10 depicted in FIG. 1 can be used to contact the insoluble planar substrate with the nucleotide composition dissolved in the solvent including the organic salt. The array synthesis system 10 shown in FIG. 1 includes a substrate station 12 on which can be mounted a substrate 14. Substrate station 12 can include a vacuum chuck connected to a suitable vacuum source (not shown) to retain a substrate 14 without exerting too much pressure thereon, since substrate 14 is often made of glass. In addition, the array synthesis system 10 includes a dispensing head 16. The dispensing head 16 can be positioned to face the substrate station 12 by a positioning system. The positioning system includes a carriage connected to substrate station 12, a first transporter controlled by a processor, and a second transporter controlled by processor. The first transporter and carriage are used to execute one axis positioning of the substrate station 12 facing the dispensing head 16 by moving substrate station 12 in the x-axis direction, while the second transporter is used to provide y- and z-axis direction adjustment. Further, once substrate station 12 has been positioned facing dispensing head 12, the positioning system will be used to scan the dispensing head 12 across the mounted substrate 14, typically line by line (although other scanning configurations could be used).

The dispensing head 12 can be of a type commonly used in an ink jet type of printer and can, for example, have multiple drop dispensing orifices communicating with one or more chambers for holding either previously obtained solution including the organic salt as a solvent/co-solvent. Ejectors are positioned in the one or more chambers, each opposite a corresponding orifice. For example, each ejector can be in the form of an electrical resistor operating as a heating element under control of a processor (although piezoelectric elements could be used instead). Each orifice with its associated ejector and portion of the chamber, defines a corresponding pulse jet. In this manner, application of a single electric pulse to an ejector causes a droplet to be dispensed from a corresponding orifice. In particular, the dispensing head is an industrial inkjet print head.

Following contact of the substrate with the solution including the organic salt as a solvent/co-solvent for a period of time and under conditions sufficient for the nucleotide composition to react with the biomolecule on the substrate or with the substrate itself, as described above, the surface of the resultant array can be further processed as desired in order to prepare the array for use. For example, further iterations of the synthesis cycle can be performed for in situ synthesis. As another example, the array surface can be washed to removed unbound reagent (e.g. unreacted polymer, and the like). Any convenient wash solution and protocol can be employed (e.g. flowing an aqueous wash solution, e.g. water, methanol, acetonitrile, and the like) across the surface of the array, etc. The surface can also be dried and stored for subsequent use, etc.

Still other methods and apparatus for fabrication of polynucleotide arrays using solutions including organic salts are described in, e.g. U.S. Pat. No. 6,242,266 to Schleiffer et al., which describes a fluid dispensing head for dispensing droplets onto a substrate, and methods of positioning the head in relation to the substrate. U.S. Pat. No. 6,180,351 to Cattell and U.S. Pat. No. 6,171,797 to Perbost describe additional methods useful for fabricating polynucleotide arrays. Methods for fabrication of arrays can include, for example, using a pulse jet such as an inkjet type head to deposit a droplet of reagent solution for each feature. Such a technique has been described, for example, in PCT publications WO 95/25116 and WO 98/41531, and elsewhere. In such methods, the head has at least one jet which can dispense droplets of a fluid onto a substrate, the jet including a chamber with an orifice, and including an ejector which, when activated, causes a droplet to be ejected from the orifice. The head can be of a type commonly used in inkjet printers, in which a plurality of pulse jets (such as those with thermal or piezoelectric ejectors) are used, with their orifices on a common front surface of the head. The head is positioned with the orifice facing the substrate. Multiple fluid droplets (where the fluid comprises the nucleotide monomer, oligonucleotide, or polynucleotide dissolved in the solvent comprising an ionic liquid) are dispensed from the head orifice so as to form an array of droplets on the substrate (this formed array may or may not be the same as the final desired array since, for example, multiple heads can be used to form the final array and multiple passes of the head(s) may be required to complete the array).

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and can be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

It should be specifically understood, though, that the present disclosure is not limited to pulse jet type deposition systems. In particular, any type of array fabricating apparatus can be used to contact the substrate with the solution including the organic salt as a solvent/co-solvent, including those such as described in U.S. Pat. No. 5,807,522, or an apparatus that can employ photolithographic techniques for forming arrays of moieties, such as described in U.S. Pat. Nos. 5,143,854 and 5,405,783, or any other suitable apparatus which can be used for fabricating arrays of moieties. For example, robotic devices for precisely depositing aqueous volumes onto discrete locations of a support surface, i.e., arrayers, are also commercially available from a number of vendors, including: Genetic Microsystems; Cartesian Technologies; Beecher Instruments; Genomic Solutions; and BioRobotics. Other methods and apparatus are described in U.S. Pat. Nos. 4,877,745; 5,338,688; 5,474,796; 5,449,754; 5,658,802; and 5,700,637. Patents and patent applications describing arrays of biopolymeric compounds and methods for their fabrication include: U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,695; 5,624,711; 5,639,603; 5,658,734; WO 93/17126; WO 95/11995; WO 95/35505, WO 97/14706, WO 98/30575; EP 742 287; and EP 799 897. See also Beier et al. "Versatile derivatisation of solid support media for covalent bonding on DNA-microchips", Nucleic Acids Research (1999) 27: 1970-1977.

EXAMPLES

In an attempt to define new solvent systems that will support both phosphoramidite chemistry and the jetting process from industrial print heads, several compositions have been developed that employ organic salts solution as enhancing agents, for example, viscosity enhancing agents. Not only do a variety of simple organic salts act to augment the viscosity of phosphoramidite friendly solvents, but they also support the coupling reaction as either pure solvents or high concentration solutes. The organic salts are also readily modified to instill other favorable qualities for use as solvents. In particular, homologous series of N,N-dialkylimidazolium and N-alkyl pyridinium salts have been found to have a wide range of viscosities and surface tensions as well as contact angles with standard glass substrates that are conducive to controlled substrate delivery. Several families of these imidazolium and pyridinium salts are also fully miscible with the standard organic solvents that support phosphoramidite chemistry such as acetonitrile, diethyl carbonate, propylene carbonate, butyronitrile, propanenitrile, adiponitrile, N-methylpyrrolidinone, and combinations thereof. Many of the organic salts also exist as room temperature liquids with no measurable vapor pressure, allowing for delivery of picoliter sized drops, which do not evaporate upon jetting. Finally, an imidazolium salt has been developed that acts as the acid catalyst required for efficient phosphoramidite coupling. This activating organic salt is also characterized by favorable viscosity, surface tension, and solubility characteristics, which make it an ideal solvent or co-solvent.

Synthesis of organic salts: In several cases, the bromide or chloride salts of a desired imidazolium or pyridinium cation were commercially available and used as starting materials. Other salts required preparation from 1-methylimidazole and a variety of alkyl halides. In a typical preparation, 309 g (300 mL, 3.76 mol) 1-methylimidazole was combined with 1160 g (1.5 equiv., 5.65 mol) 1-chlorododecane and about 200 mL 1,4-dioxane in a 2.0 L flask. The reaction flask was fitted with a cooling tower and purged with argon before being heated to 90-100° C. for 6 days. The reaction was then cooled and excess dioxane was removed by rotary evaporation. The resulting viscous oil was dissolved in approx. 1.0 L methanol and was subsequently washed in 300 mL portions no less than 5× with 1.0 L of hexanes. Once $^1$H-NMR indicated complete removal of 1-chlorododecane, the methanolic solutions were pooled and concentrated via rotary evaporation to yield an off white solid (961 g, about 89%). Half (480 g) of this solid was dissolved in deionized $H_2O$ and transferred to 2.0 L separatory funnel. To this solution was added a second aqueous solution of Lithium bis(trifluoromethylsulfonyl)imide (1.1 equivalent, 530 g). A biphasic system instantly developed, consisting of an aqueous phase and a more dense phase composed of the 3-dodecyl-1-methylimidazolium bis(trifluoromethylsulfonyl)imide (12mim TFSI) salt as an ionic liquid. About 600 mL dichloromethane was added and the separatory funnel was shaken vigorously. The organic layer was collected and washed 5× with deionized $H_2O$. The washed organic layer was then collected and excess dichloromethane was removed via rotary evaporation to yield a viscous brown liquid which was further dried under high vacuum (<500 μm Hg) at 60° C. for 2 h. The bulk liquid was transferred to a nalgene bottle and dried with activated 3 Å molecular seives until Karl Fischer titration indicated <30 ppm $H_2O$.

In another preparation, 150 mL (1.88 mol) 1-methylimidazole was dissolved in 1.5 equiv. (390 g, 303 mL) 1-bromobutane in a 1.0 L erlenmeyer flask. The solution was sonicated in a fume hood until it began to boil (~30 min). Sonication was stopped and the reaction mixture allowed to cool for 30 min. Sonication was repeated for an additional 45 min and the resulting viscous liquid was transferred to a round bottom flask. Excess 1-bromobutane was removed by rotary evaporation and the resulting oil was dissolved in deionized $H_2O$ and washed 2× with ethyl acetate to remove unreacted 1-methylimidazole. Conversion to the bis(trifluoromethylsulfonyl)imide salt was performed as described above, based on 85% conversion of 1-methylimidazole to the 3-butyl-1-methylimidazolium bromide (yield determined by $^1$H-NMR spectrum of crude sonicated product before washing with ethyl acetate). The final product (bmim TFSI) was a clear viscous liquid.

The activating salt (1-methylimidazolium bis(trifluoromethylsulfonyl)imide; Hmim TFSI) was prepared in a similar manner by dissolving 300 mL (3.76 mol) 1-methylimidazole in an aqueous solution of 1.2 equiv. (622 g, 4.51 mol) $NaH_2PO_4$ in a separatory funnel. This solution was used directly in the conversion to the bis(trifluoromethylsulfonyl) imide salt as described above. The final product (Hmim TFSI) was isolated as a clear viscous liquid but was observed to form a crystalline wax in an unpredictable manner upon several days of standing. The wax was readily melted by heating to 60° C.

Physical Properties: Several of the physical properties have been examined for a series of 3-alkyl-1-methylimidazolium salts, where the variable alkyl group ranges in length from ethyl to dodecyl. These cations were originally pursued on account of their propensity to form room temperature organic salts when paired with certain anions.

Other organic salts that were pursued were readily dissolved in solvents known to support phosphoramidite chemistry, were not reactive with or destructive of the reagents, and could be readily dried and used with minimal precaution in sample preparation.

An exemplary anion yielded salts that not only fulfilled these requirements, but also resulted in useful modification of the viscosities, surface tensions, and contact angles of a variety of solvents. The bis(trifluoromethylsulphonyl)imide anion (hereafter referred to as TFSI) imparted all of these properties and invariably yielded room temperature liquids when paired with 3-alkyl-1-methylimidazolium cations. The TFSI anion also gave pyridinium salts which, while room temperature solids, could be added to various solvents as modifiers of viscosity, surface tension, and contact angle. The TFSI salt of the protonated 1-methylimidazolium cation also yields a low melting solid that can act as a physical property (i.e. viscosity, surface tension, and contact angle) modifier, and as an activator of phosphoramidite coupling.

The 3-alkyl-1-methylimidazolium bis(trifluorosulfonyl) imide (Amim TFSI) salts are shown as examples here of the range of physical properties encountered amongst simple organic salts. Several of these salts were prepared and evaluated, including 3-ethyl-1-methylimidazolium TFSI (Emim TFSI), 3-butyl-1-methylimidazolium TFSI (Bmim TFSI), 3-octyl-1-methylimidazolium TFSI (Omim TFSI), and 3-dodecyl-1-methylimidazolium TFSI (12mim TFSI). As mentioned before, the activating salt, 1-methylimidazolium TFSI (Hmim TFSI) was also prepared. The temperature dependant viscosity of several of the salts was measured, as was the surface tension and contact angle on the glass substrate. Each parameter will be addressed in turn.

Viscosities of the various solvents were determined under the indicated conditions using a Brinkmann Lauda RC6 CS temperature controlled water circulation bath attached to the insulated sleeve of a Thermo Haake VT 550 rotating barrel viscometer. The viscosity of the pure Amim TFSI ionic liquids was seen to vary with temperature to different degrees, depending on the length of the alky chain, as shown in Table 1. Mixtures of these salts with solvents such as propylene carbonate and diethylene carbonate give roughly average visocsities based on a mole/mole ratio. These mixtures can be used to obtain solvents that support coupling and fall in the window of viscosity values which will successfully jet from the print head (roughly 8-12 cP). The shorter chain derivatives (Emim and Bmim) are more stable to temperature changes in the examined range and can be more useful in the development of temperature stable formulations. The greater temperature variability of the longer chain derivatives (Omin and 12minm) may afford utility in applications where the nature of the solvent must change with temperature.

TABLE 1

Temperature dependance of viscosity of 3-alkyl-1-methylimidazolium salts.

|  | Hmim TFSI | Emim TFSI | Bmim TFSI | Omim TFSI | 12mim TFSI |
|---|---|---|---|---|---|
| 20° C. |  | 39.2 cP | 66.1 cP | 115 cP | 184 cP |
| 22.5° C. |  | 37.2 cP | 58.8 cP | 102 cP | 165 cP |
| 25° C. | 42.5 cP* | 34.1 cP | 53.5 cP | 90.5 cP | 144 cP |
| 27.5° C. |  | 31.3 cP | 48.4 cP | 80.1 cP | 127 cP |
| 30° C. |  | 29.1 cP | 43.9 cP | 72.0 cP | 112 cP |
| 32.5° C. |  | 26.6 cP | 40.0 cP | 64.1 cP | 99.7 cP |
| 35° C. |  | 24.6 cP | 36.7 cP | 57.4 cP | 89.3 cP |
| 60° C. | 13.3 cP |  |  |  |  |

*Hmim TFSI can be isolated and manipulated as a room temperature liquid, but will spontaneously crystallize after time.

Contact angles were determined by direct observation under high magnification of the interface between the glass substrate and 1-3 mm droplets of the solvent in question. Attempts were also made to measure the contact angle of the solvents on a gold surface, but the gold substrates were of questionable quality and the value of the numbers obtained was dubious. The contact angle on gold is important for the jetting process, where the orifice of the inkjet head is coated with an inert layer of gold. On the glass substrate (Table 2), contact angles of ~90° are ideal, with significantly lower angles leading to poor control of substrate printing and significantly larger angles leading to inadequate surface contact. Solvent systems with contact angles in the range of ~70 to 110 can be expected to show greater utility in the printing process.

TABLE 2

Contact angles of various solvents on functionalized glass chips at 22° C.

|  | 1 | 2 | 3 | Mean |
|---|---|---|---|---|
| 12mim TFSI | 50 | 50 | 51 | 50 |
| Omim TFSI | 53 | 55 | 54 | 54 |
| Bmim TFSI | 61 | 63 | 62 | 62 |
| Hmim TFSI | 74 | 72 | 72 | 73 |
| DEC | 24 | 24 | 24 | 24 |
| PC | 64 | 65 | 65 | 65 |
| Hmim/DEC | 55 | 60 | 58 | 58 |

PC = propylene carbonate;
DEC = diethylene carbonate;
Hmim/DEC = 1:1 mole/mole mixture of Hmim TFSI and DEC, viscosity ~10 cP.

Surface tensions of the various 3-alkyl-1-methylimidazolium TFSI salts have been previously reported in the literature (Dzyuba, S. V., Bartsch, R. A., *Chem. Phys. Chem.*, 3, 161-166, 2002). The surface tensions are seen to vary from <30 mN/m for the longer alkyl chain derivatives (Omim TFSI, 12mim TFSI) to about 40 mN/m for the Emim TFSI salt. This trend is the inverse of that seen for viscosity, which is seen to increase with increasing alkyl chain length. The surface tension of the activating Hmim TFSI salt was measured using a Dataphysics DCAT tensiometer employing the Du Nuoy ring method. Its value (38.2 mN/m) was found to fall in the middle of the range of the alkyl substituted 1-methylimidazolium salts. For efficient jetting, surface tensions in the range of 35 to 45 are currently viewed as acceptable for our purposes. The surface tensions of solvent systems can be readily be modified by mixing various ratios of soluble organic salts with other solvents which support phosphoramidite coupling. For instance, various proportions of propylene carbonate (surface tension about 45 mN/m), diethylene carbonate (surface tension about 28 mN/m) and Hmim TFSI (surface tension about 38 mN/m) have been shown to give solvents with viscosities in the acceptable range and surface tensions between 35 mN/m and 45 mN/m.

$^{31}$P-NMR coupling studies: Data were obtained on a 400 MHz Varian Unity Inova spectrometer equipped with an ASW multi nucleus probe and Sun workstation. In a typical experiment, phosphoramidite was dissolved to a concentration of 100 mM in the presence of excess 5'-dimethoxytritylthymidine or 3'-acetylthimidine in either a pure ionic liquid or an appropriate mixture of an organic salt and co-solvent. $^{31}$P-NMR was used to determine stability of the phosphoramidite under these conditions. Once the stability of this mixture was determined, the activator (Hmim TFSI) was added either as a pure salt or in solution with a co-solvent to a final concentration of about 5-50%. $^{31}$P-NMR was then used to determine the efficiency of the coupling reaction.

Figure 2:
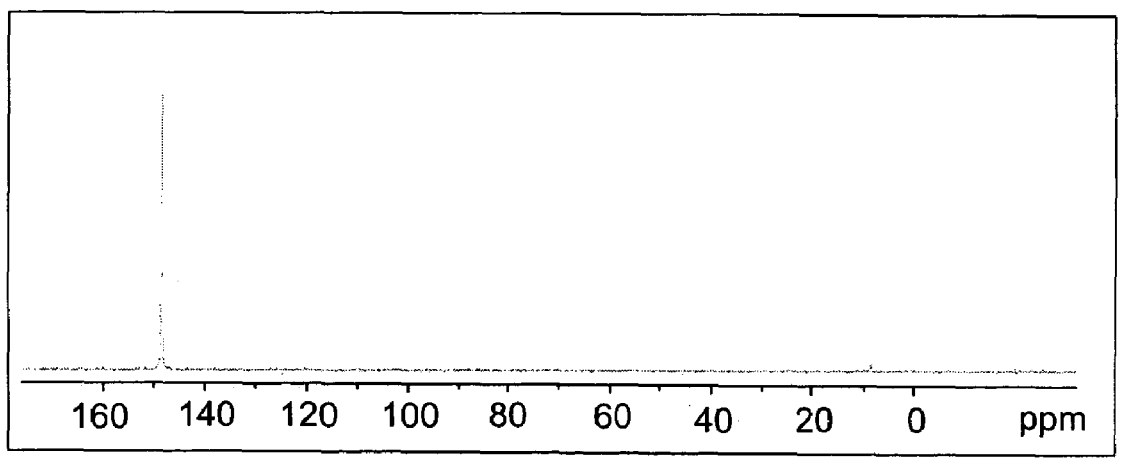
FIG. 2 depicts an NMR scan of thymidine phosphoramidite (100 mM) and excess 3'-acetylthymidine dissolved in N-ethylpyridinium trifluoromethylsulfonyl imide (TFSI) ionic liquid.

FIG. 2 illustrates shows a typical outcome for a solvent system that supports phosphoramidite coupling. A variety of salts based on imidazolium and pyridinium cations were observed to support the coupling reaction. Also, several anions were also found to be compatible with phosphoramidite coupling. In the examples below, N-ethylpyridinium TFSI is shown to support coupling, as is the trifluoromethanesulfonyl (triflate) salt of the Bmim cation. As a whole, all of the salts tested which were not subject to the limitations of solubility, reactivity, or stability as outlined above supported the coupling reaction. Phosphoramidites were found to be soluble to concentrations of at least 100 mM in all of the pure ionic liquids that were found to support coupling, as well as in all mixed solvent systems comprised of organic salts and co-solvents.

FIG. 2 depicts an NMR scan of thymidine phosphoramidite (100 mM) and excess 3'-acetylthymidine dissolved in N-ethylpyridinium TFSI ionic liquid. The peak seen at ~148 ppm corresponds to the unreacted phosphoramidite.

Figure 3:
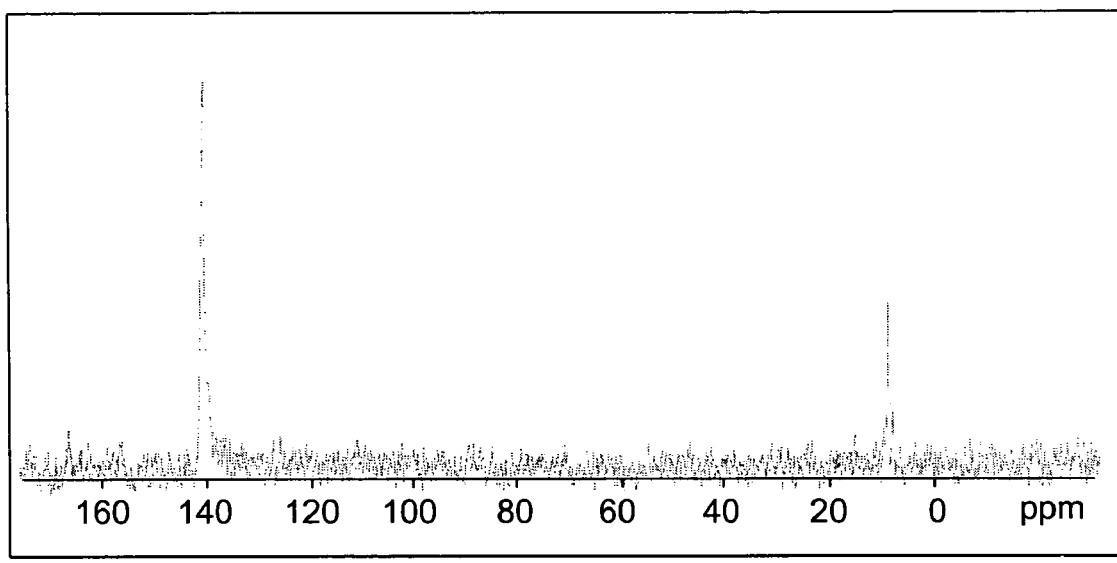
FIG. 3 depicts an NMR scan of thymidine phosphoramidite (100 mM) and excess 3'-acetylthymidine dissolved in N-ethylpyridinium TFSI ionic liquid after addition of 5% (v/v) of the methylimidazolium (Hmim) TFSI activator.

FIG. 3 depicts an NMR scan of thymidine phosphoramidite (100 mM) and excess 3'-acetylthymidine dissolved in N-ethylpyridinium TFSI ionic liquid after addition of 5% (v/v) of the Hmim TFSI activator. The peak at ~140 ppm corresponds to the phosphite triester product. The peak at ~15 ppm corresponds to the H-phosphonate.

Figure 4:
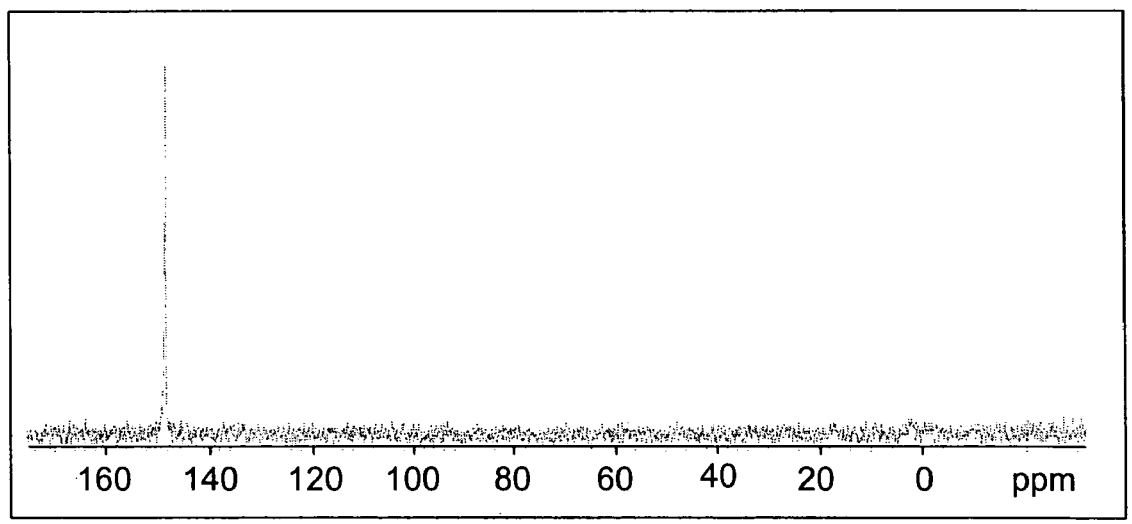
FIG. 4 depicts an NMR scan of thymidine phosphoramidite (100 mM) and excess 3'-acetylthymidine dissolved in 3-butyl-1-methylimidazolium triflate ionic liquid.

FIG. 4 depicts an NMR scan of thymidine phosphoramidite (100 mM) and excess 3'-acetylthymidine dissolved in 3-butyl-1-methylimidazolium triflate ionic liquid. The peak seen at ~148 ppm corresponds to the unreacted phosphoramidite.

Figure 5:
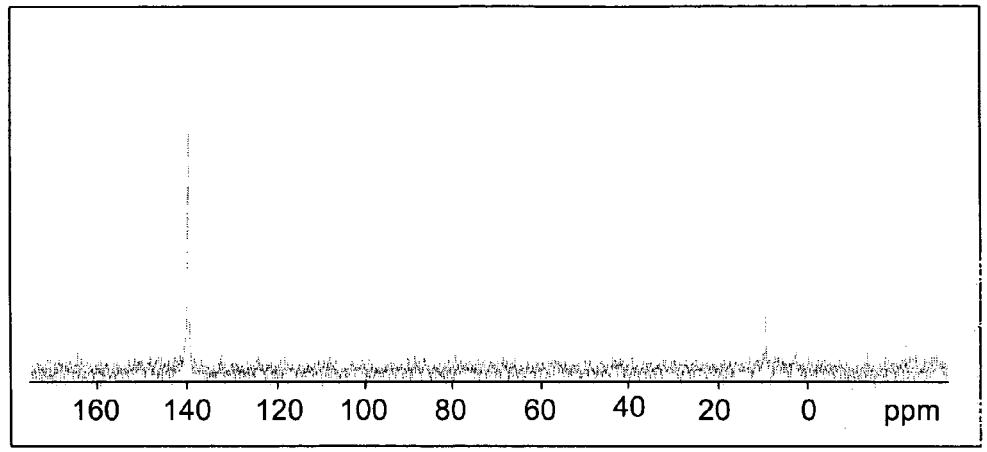
FIG. 5 depicts an NMR scan of thymidine phosphoramidite (100 mM) and excess 3'-acetylthymidine dissolved in 3-butyl-1-methylimidazolium triflate ionic liquid after addition of 5% (v/v) of the Hmim TFSI activator.

FIG. 5 depicts an NMR scan of thymidine phosphoramidite (100 mM) and excess 3'-acetylthymidine dissolved in 3-butyl-1-methylimidazolium triflate ionic liquid after addition of 5% (v/v) of the Hmim TFSI activator. The peak at ~140 ppm corresponds to the phosphite triester product. The peak at ~15 ppm corresponds to the H-phosphonate.

Synthesis of oligomeric DNA in pure organic salts and solvent mixtures: Two methods were employed to demonstrate the suitability of organic salts as solvents for solid phase phosphoramidite coupling. First, a manual synthesis was developed whereby syringes were used to deliver solutions of phosphoramidites, organic salts, and activators to functionalized CPG-500 synthesis columns. In a typical synthesis, phosphoramidite was dissolved to a concentration of 100 mM in either a pure ionic liquid or in a mixture of an organic salt and a co-solvent (dried to <30 ppm H$_2$O) to yield "solution A". The activator, Hmim TFSI, was then dissolved in the same ionic liquid or co-solvent (dried to <30 ppm H2O) to a concentration of 5-50% to yield "solution B". Aliquots of 300 µL were drawn from solution A and solution B into two separate syringes and these syringes were fitted to the ends of a 1.0 µmol DNA synthesis column. The plungers on the two syringes were then alternately compressed and drawn out to allow for 1.0 to 2.0 min continuous flow of reagents over the CPG substrate. After the coupling step was completed, the CPG was washed with 5 mL acetonitrile and the remainder of the synthetic cycle was completed on an ABI 392 DNA synthesizer, as described below. In other manual coupling experiments, the phosphoramidite was dissolved in a solution containing the Hmim TFSI activator and this activated solution was used directly for coupling.

The second method employed the ABI 392 DNA synthesizer for the entire synthetic sequence. Phosphoramidites were dissolved in solutions of an organic salt and an appropriate co-solvent to yield solutions of sufficiently low viscosity (<10 cP) to readily allow for flow through the synthesizer channels. In some experiments, an activator was added to the phosphoramidite solutions, which precluded the need for subsequent mixing with a discrete activator solution. Standard synthetic protocols were used, employing sufficient solvent washes and channel flushes after each step. The only variable step in each synthesis was the time allotted for the coupling step reagents to fill the reaction column. The viscosity of each solvent mixture varied enough to alter the time required to deliver the reagents. Therefore, each reagent mixture was timed to determine how long it would take to completely fill the reaction column. This predetermined time was then used for each coupling step in the synthetic sequence. No capping step was employed in any of the syntheses. All steps other than the coupling sequence was also used for the manually coupled substrates described above. A typical synthesis included the following steps:

| | |
|---|---|
| Trityl deblock | 85 sec |
| Phosphoramidite delivery | variable fill time, as determined by solvent viscosity |
| Static coupling | 1.0 to 3.0 min |
| Iodine oxidation | 20 sec |
| Cleavage from the solid support was achieved by 12 h treatment with 40% aqueous ammonia at 60° C. | |

Reverse phase HPLC was employed to analyze the products. Data were collected on an Agilent 1100 HPLC and workstation running the Agilent Chemstation™ software suite. Gradients of acetonitrile and 50 mM triethyl ammonium acetate or 50 mM triethyl ammonium bicarbonate were used to elute the products from a 4.0×250 mm Agilent Hypercil ODS™ 5 µm reverse phase column. Below are several examples of DNA oligomers prepared in pure ionic liquids (2-ethyl-1-methylimidazolium TFSI) or in mixtures of organic salts with either diethylene carbonate or propylene carbonate.

Figure 6:
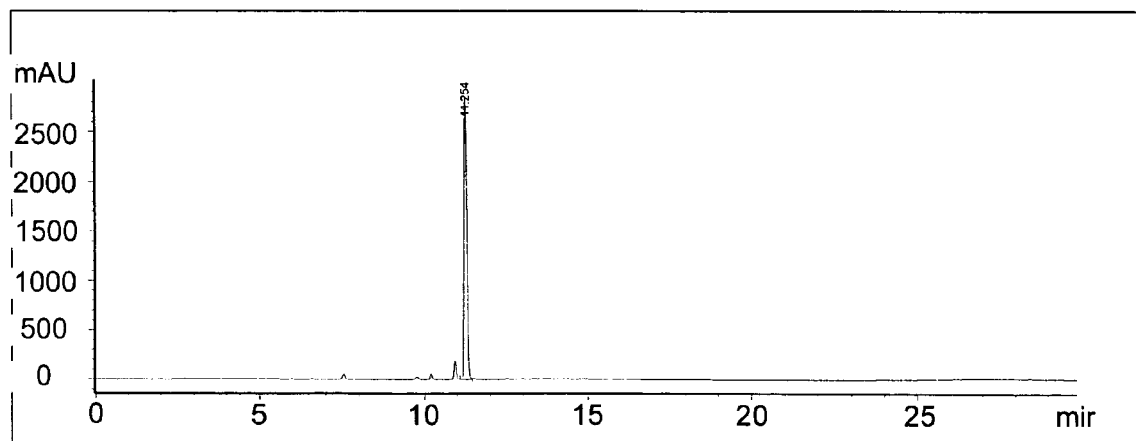
FIG. 6 depicts an NMR scan of T4 prepared via manual coupling protocol described below.

FIG. 6 depicts an NMR scan of T4 prepared via manual coupling protocol described above. Phosphoramidites were dissolved to 100 mM in a roughly 1:1 (v/v) mixture of 12mim TFSI and propylene carbonate. Coupling to the growing oligomer was activated by concurrent introduction of 200 µL of the phosphoramidite solution with a 200 µL of a 1:1 (v/v) mixture of Hmim TFSI and propylene carbonate followed by 2.0 min of continuous solvent flow through the column.

Figure 7:
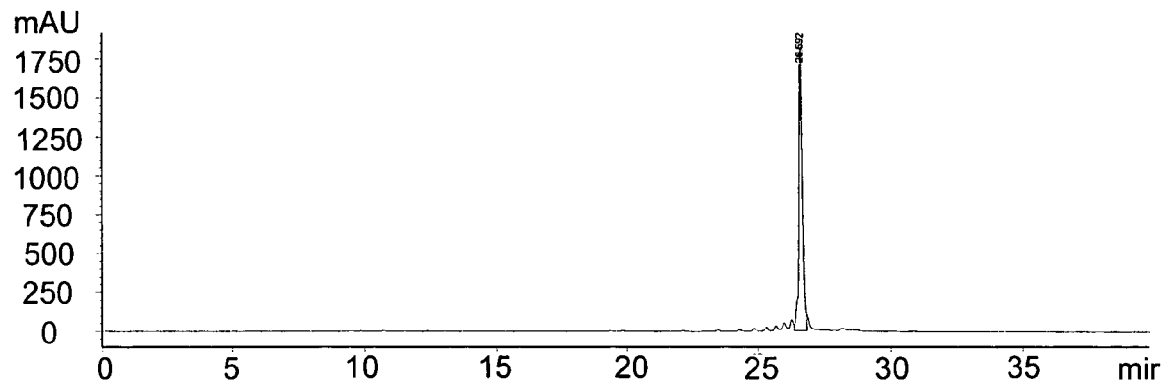
FIG. 7 depicts an NMR scan of T12 prepared on the ABI 392 DNA synthesizer by the protocol described below.

FIG. 7 depicts an NMR scan of T12 prepared on the ABI 392 DNA synthesizer by the above protocol. Phosphoramidite was dissolved to 100 mM in 75% diethylene carbonate and 25% Hmim TFSI (v/v), which served as co-solvent and activator. The solvent system had a final viscocity of ~7 cP and was delivered directly to the column without further dilution or activation. A 2.0 min coupling time was used to give results comparable to coupling in acetonitrile.

Figure 8:
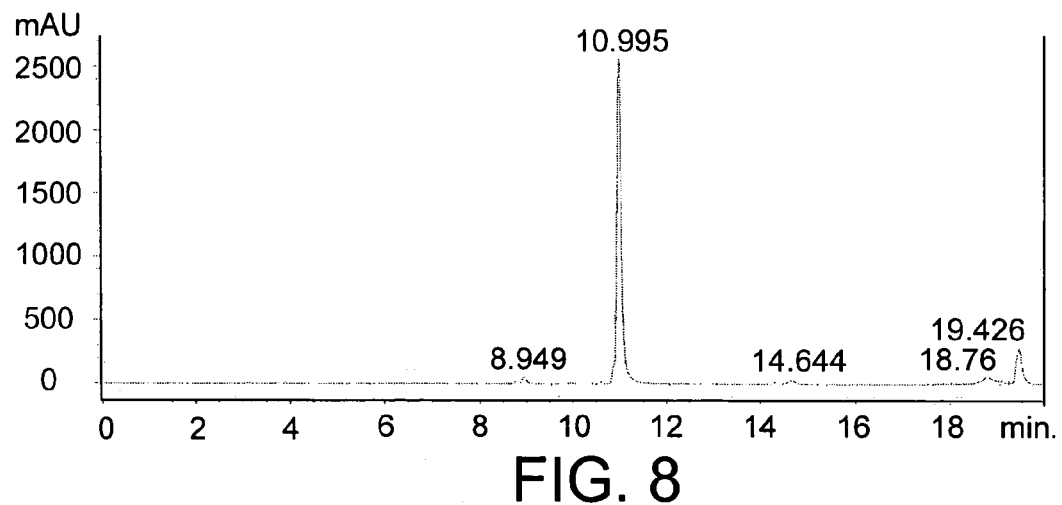
FIG. 8 depicts an NMR scan of T4 prepared via the manual coupling by the protocol described below.

FIG. 8 depicts an NMR scan of T4 prepared via the manual coupling protocol described above. The phosphoramidite was dissolved to 100 mM in 300 µL pure Emim TFSI ionic liquid. This solution was concurrently delivered to a synthesis column with 300 µL solution of 0.25 M dicyanoimidazole activator dissolved in Emim TFSI.

While the foregoing embodiments have been set forth in considerable detail for the purpose of making a complete disclosure of the invention, it will be apparent to those of skill in the art that numerous changes can be made in such details without departing from the spirit and the principles of the disclosure. Accordingly, the disclosure should be limited only by the following claims.

All patents, patent applications, and publications mentioned herein are hereby incorporated by reference in their entireties.

What is claimed is:

1. A method of forming an addressable nucleotide array, comprising providing a first nucleotide compound selected from a nucleotide, an oligonucleotide, and a polynucleotide, wherein the first nucleotide compound is dissolved in a first solution including a first co-solvent and a second co-solvent, wherein the first co-solvent comprises an organic salt, wherein the organic salt comprises a substituted heterocyclic organic cation and an anion, wherein the organic salt has a pKa of about 6 to 8, wherein the organic salt does not reduce the reaction characteristics of the first solution, wherein the first solution has a viscosity of about 5 to 20 cP and a surface tension of about 25 to 45 mN/m at a temperature of about 30 to 40° C.;

disposing the first solution onto a first position on a substrate, wherein a structure is disposed in the first position, wherein the structure has a second nucleotide compound disposed thereon, wherein the second nucleotide compound is selected from a nucleotide, an oligonucleotide, and a polynucleotide; and disposing a second solution on the first position of the substrate, wherein the second solution includes an activator, wherein the activator initiates the formation of a third nucleotide compound that includes the first nucleotide compound and the second nucleotide compound.

2. The method of claim 1, wherein the anion is selected from chloride methylsulfate ($CH_3SO_4^-$), trifluoroacetate ($CF_3CO_2^-$), heptafluorobutanoate ($CF_3(CF_2)_2CO_2^-$), triflate ($CF_3SO_2^-$), nonaflate ($C_2F_5SO_2^-$), tosylate anion, dicyanimide anion, bis(trifluoromethylsulfonyl)imide (($CF_3SO_2)_2N^-$), bis(perfluoroethylsulfonyl)imide (($C_2F_5SO_2)_2N^-$), tris(trifluoromethylsulfonyl)methide (($CF_3SO_2)_3C^-$), and combinations thereof.

3. The method of claim 1, wherein the cation is an N-substituted pyridine having the formula

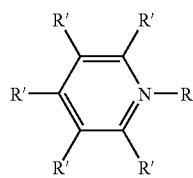

wherein R is alkyl and each R' is independently selected from a hydrido, an alkyl, and a halogen group.

4. The method of claim 1, wherein the cation has the formula

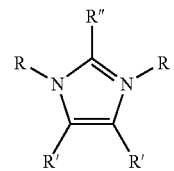

wherein each R is independently selected from an alkyl, each R' is independently selected from a hydrido, an alkyl, and a halogen, and R" is selected from a hydrido and a methyl.

5. The method of claim 1, wherein the cation is a 1,3 di-substituted imidazole organic cations selected from 1,3-dimethyl-imidazolium, 1-ethyl-3-methyl-imidazolium, 1-butyl-3-methyl-imidazolium, 1-hexyl-3-methyl-imidazolium, 1-decyl-3-methyl-imidazolium, 1-dodecyl-3-methyl-imidazolium, 1-methyl-3-octyl-imidazolium, 1-methyl-3-tetradecyl-imidazolium, 1,2-dimethyl-3-propyl-imidazolium, 1-ethyl-2,3-dimethyl-imidazolium, 1-butyl-2,3-dimethyl-imidazolium.

6. The method of claim 1, wherein the solution has a viscosity of about 15 to 20 cP and a surface tension of about 20 to 30 mN/m at a temperature of about 30 to 40° C.

7. The method of claim 1, wherein disposing the first solution is conducted using an inkjet printhead.

8. The method of claim 1, wherein the second co-solvent is selected from acetonitrile, propylene carbonate, adiponitrile, ethylene carbonate, diethyl carbonate, and combinations thereof.

9. The method of claim 1, wherein the second co-solvent is selected from tetrahydrofuran, dimethylformamide, methylene chloride, adiponitrile, toluene, dioxane, dimethylsulfoxide, succinonitrile, N-methyl pyrrolidone, sulfolane, nitromethane, nitrobenzene, and combinations thereof.

10. The method of claim 1, further comprising:
a) disposing a fourth nucleotide compound onto the first position on the substrate, wherein the fourth nucleotide compound is selected from a nucleotide, an oligonucleotide, and a polynucleotide, wherein the fourth nucleotide compound is dissolved in a fourth solution including the first co-solvent and the second co-solvent, wherein the first co-solvent comprises the organic salt, wherein the fourth solution has a viscosity of about 5 to 20 cP and a surface tension of about 25 to 45 at a temperature of about 30 to 40° C.;
b) disposing the second solution on the first position of the substrate, wherein the activator initiates the formation of a fifth nucleotide compound that includes the first nucleotide compound, the second nucleotide compound, and the fourth nucleotide compound; and
c) repeating steps a) and b) to form a target nucleotide compound.

11. The method of claim 10, wherein the activator is an organic salt, wherein the organic salt comprises a substituted heterocyclic organic cation and an anion.

12. The method of claim 11, wherein the organic salt is methylimidazolium (trifluoromethylsulfonyl)imide.

13. The method of claim 10, wherein the solution has a contact angle from 45 to 70.

14. A method of forming an addressable nucleotide array, comprising
providing a first nucleotide compound selected from a nucleotide, an oligonucleotide, and a polynucleotide, wherein the first nucleotide compound is dissolved in a first solution including a first solvent, wherein the first solvent comprises an organic salt, wherein the organic salt comprises a substituted heterocyclic organic cation and an anion, wherein the first solution has a viscosity of about 5 to 20 cP and a surface tension of about 25 to 45 mN/m at a temperature of about 30 to 40° C.;

disposing the first solution onto a first position on a substrate, wherein a structure is disposed in the first position, wherein the structure has a second nucleotide compound disposed thereon, wherein the second nucleotide compound is selected from a nucleotide, an oligonucleotide, and a polynucleotide; and disposing a second solution on the first position of the substrate, wherein the second solution includes an activator, wherein the activator initiates the formation of a third nucleotide compound that includes the first nucleotide compound and the second nucleotide compound.

15. The method of claim 14, wherein the anion selected from chloride methylsulfate ($CH_3SO_4^-$), trifluoroacetate ($CF_3CO_2^-$), heptafluorobutanoate ($CF_3(CF_2)_2CO_2^-$), triflate ($CF_3SO_2^-$), nonaflate ($C_2F_5SO_2^-$), tosylate anion, dicyanimide anion, bis(trifluoromethylsulfonyl)imide (($CF_3SO_2)_2N^-$), bis(perfluoroethylsulfonyl)imide (($C_2F_5SO_2)_2N^-$), tris(trifluoromethylsulfonyl)methide (($CF_3SO_2)_3C^-$), and combinations thereof.

16. The method of claim 14, wherein the cation is an N-substituted pyridine having the formula

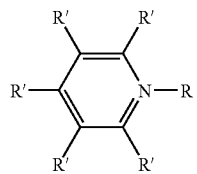

wherein R is alkyl and each R' is independently selected from a hydrido, an alkyl, and a halogen group.

17. The method of claim 14, wherein the cation has the formula

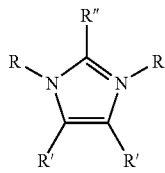

wherein each R is independently selected from an alkyl, each R' is independently selected from a hydrido, an alkyl, and a halogen, and R" is selected from a hydrido and a methyl.

18. The method of claim 14, wherein the cation is a 1,3di-substituted imidazole organic cations selected from 1,3-dimethyl-imidazolium, 1-ethyl-3-methyl-imidazolium, 1-butyl-3-methyl-imidazolium, 1-hexyl-3-methyl-imidazolium, 1-decyl-3-methyl-imidazolium, 1-dodecyl-3-methyl-imidazolium, 1-methyl-3-octyl-imidazolium, 1-methyl-3-tetradecyl-imidazolium, 1,2-dimethyl-3-propyl-imidazolium, 1-ethyl-2,3-dimethyl-imidazolium, 1-butyl-2,3-dimethyl-imidazolium, and combinations thereof.

19. The method of claim 14, wherein the solution has a viscosity of about 15 to 20 cP and a surface tension of about 20 to 30 mN/m at a temperature of about 30 to 40° C.

20. The method of claim 14, wherein disposing the first solution is conducted using an inkjet printhead.

21. The method of claim 14, wherein the organic salt has a pKa of about 6 to 8.

22. An inkjet printhead solvent, comprising: an organic salt including a substituted heterocyclic organic cation and an anion, wherein the organic salt has a pKa of about 6 to 8, wherein the first solution has a viscosity of about 5 to 20 cP and a surface tension of about 25 to 45 mN/m at a temperature of about 30 to 40° C., wherein a first nucleotide compound is dissolved in a first solution including the organic salt.

23. The inkjet printhead solvent of claim 22, wherein the cation is an N-substituted pyridine having the formula

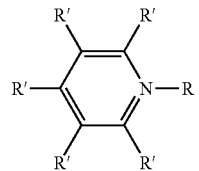

wherein R is alkyl and each R' is independently selected from a hydrido, an alkyl, and a halogen group.

24. The inkjet printhead solvent of claim 22, wherein the cation has the formula

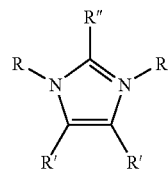

wherein each R is independently selected from an alkyl, each R' is independently selected from a hydrido, an alkyl, and a halogen, and R" is selected from a hydrido and a methyl.

25. The inkjet printhead solvent of claim 22, wherein the cation is a 1,3 di-substituted imidazole organic cations selected from 1,3-dimethyl-imidazolium, 1-ethyl-3-methyl-imidazolium, 1-butyl-3-methyl-imidazolium, 1-hexyl-3-methyl-imidazolium, 1-decyl-3-methyl-imidazolium, 1-dodecyl-3-methyl-imidazolium, 1-methyl-3-octyl-imidazolium, 1-methyl-3-tetradecyl-imidazolium, 1,2-dimethyl-3-propyl-imidazolium, 1-ethyl-2,3-dimethyl-imidazolium, 1-butyl-2,3-dimethyl-imidazolium, and combinations thereof.

26. The inkjet printhead solvent of claim 22, wherein the anion is selected from chloride methylsulfate ($CH_3SO_4^-$), trifluoroacetate ($CF_3CO_2^-$), heptafluorobutanoate ($CF_3(CF_2)_2CO_2^-$), triflate ($CF_3SO_2^-$), nonaflate ($C_2F_5SO_2^-$), tosylate anion, dicyanimide anion, bis(trifluoromethylsulfonyl)imide (($CF_3SO_2)_2N^-$), bis(perfluoroethylsulfonyl)imide (($C_2F_5SO_2)_2N^-$), tris(trifluoromethylsulfonyl)methide (($CF_3SO_2)_3C^-$), and combinations thereof.

27. The inkjet printhead solvent of claim 22, further comprising a co-solvent selected from acetonitrile, propylene carbonate, adiponitrile, ethylene carbonate, diethyl carbonate, and combinations thereof.

28. The inkjet printhead solvent of claim 22, further comprising a co-solvent selected from tetrahydrofuran, dimethylformamide, methylene chloride, adiponitrile, toluene, dioxane, dimethylsulfoxide, succinonitrile, N-methyl pyrrolidone, sulfolane, nitromethane, nitrobenzene, and combinations thereof.

* * * * *